United States Patent
Riggs et al.

(10) Patent No.: US 7,442,804 B2
(45) Date of Patent: Oct. 28, 2008

(54) PROCESS FOR THE PREPARATION OF FUROPYRROLES

(75) Inventors: Richard Lewis Riggs, Edinburgh (GB); Nicholas James Westwood, Dundee (GB); David Macdonald Smith, Fife (GB); Colin Morton, Riehen (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 123 days.

(21) Appl. No.: 10/561,393

(22) PCT Filed: Jun. 28, 2004

(86) PCT No.: PCT/EP2004/051259

§ 371 (c)(1),
(2), (4) Date: Dec. 19, 2005

(87) PCT Pub. No.: WO2005/005430

PCT Pub. Date: Jan. 20, 2005

(65) Prior Publication Data

US 2007/0100135 A1      May 3, 2007

(30) Foreign Application Priority Data

Jul. 7, 2003     (EP) .................... 03405507

(51) Int. Cl.
*C07D 491/048* (2006.01)
*A61K 31/4015* (2006.01)

(52) U.S. Cl. .................... 548/453; 514/421

(58) Field of Classification Search ............ 548/453
See application file for complete search history.

(56) References Cited

U.S. PATENT DOCUMENTS 5,808,094 A * 9/1998 Mizuguchi et al. ........ 548/453
2004/0171847 A1  9/2004 Morton et al. ............. 548/453

FOREIGN PATENT DOCUMENTS

WO       03/022848      3/2003

OTHER PUBLICATIONS

U.S. Appl. No. 10/485,840, filed Feb. 2004, Colin Morton.*

Richter, et al. Microwave-Enhanced Chemistry. Analytical Chemistry. Jan. 1, 2001, pp. 30A-37A.*
Bansal, Raj. 9.6 Microwave Heating in Organic Synthesis. Synthetic Approaches in Organic Chemistry. (1996) p. 409.*

* cited by examiner

*Primary Examiner*—Kamal Saeed
*Assistant Examiner*—Shawquia Young
(74) *Attorney, Agent, or Firm*—Joseph C. Suhadolnik

(57) ABSTRACT

The present invention relates to a process for the preparation of furopyrroles of general formula (I), comprising (a) heating a compound of the formula (II) under microwave irradiation optionally in the presence of an inert solvent, wherein $A^1$ and $A^2$ are $C_1$-$C_{18}$alkyl, $C_2$-$C_{18}$alkenyl, $C_2$-$C_{18}$alkynyl, $C_5$-$C_8$cycloalkyl, $C_5$-$C_8$cycloalkenyl, aryl or heteroaryl, $A^3$ is hydrogen, $C_1$-$C_{18}$alkyl, cyanomethyl, $Ar^3$, —$CR^{30}R^{31}$—$(CH_2)_m$—$Ar^3$ or Y—$R^{32}$, wherein $R^{30}$ and $R^{31}$ independently of each other stand for hydrogen or $C_1$-$C_4$alkyl, or phenyl which can be substitute up to three times with $C_1$-$C_4$alkyl, $Ar^3$ stands for aryl, $C_5$-$C_8$ cloalkyl, $C_5$-$C_8$cycloalkenyl or heteroaryl, which can be substituted one to three times with $C_1$-$C_8$alkyl, $C_1$-$C_8$alkoxy, halogen or phenyl, which can be substituted with $C_1$-$C_8$alkyl or $C_1$-$C_8$alkoxy one to three times, and m stands for 0, 1, 2, 3 or 4, R is $C_1$-$C_{18}$alkyl, in particular $C_1$-$C_4$alkyl, aryl, in particular phenyl, or aralkyl, in particular benzyl, which can be substituted one to three times with $C_1$-$C_8$alkyl, $C_1$-$C_8$alkoxy, or halogen, Y is —C(O)—, —C(O)O—, —C(O)NH—, —$SO_2NH$— or —$SO_2$— and $R^{32}$ is $C_1$-$C_{18}$alkyl, $Ar^3$, or aralkyl. The furopyrroles of the general formula (I) can be can be obtained in high yield and high purity by the process of the present invention.

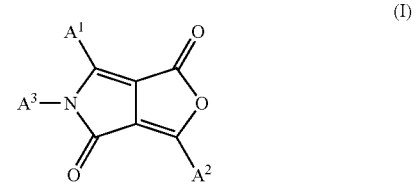

(I)

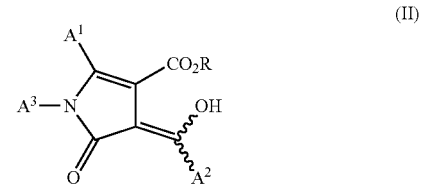

(II)

20 Claims, No Drawings

PROCESS FOR THE PREPARATION OF FUROPYRROLES

The present invention relates to a microwave assisted rapid and economical process for the preparation of furopyrroles of the general formula I, comprising (a) heating a compound of the formula II under microwave irradiation optionally in the presence of an inert solvent. The furopyrroles of the general formula I can be obtained in high yield and high purity by the process of the present invention.

WO03022848 discloses a process for the preparation of furopyrroles of the general formula I, comprising heating a compound of the formula

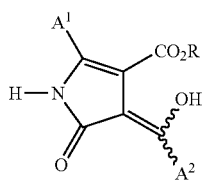

(IIa)

in an inert solvent,
wherein $A^1$ and $A^2$ have the meanings as given below and R is $C_1$-$C_{18}$alkyl, in particular $C_1$-$C_4$alkyl, aryl, in particular phenyl, or aralkyl, in particular benzyl, which can be substituted one to three times with $C_1$-$C_8$alkyl, $C_1$-$C_8$alkoxy, or halogen. Examples of inert solvents include, but are not limited to, aromatic solvents, like biphenyl, para-, meta or ortho-terphenyl, dibenzyltoluene, α-methyl- or β-methylnaphthalene, cyclic carbonates, like 1,3dioxolan-2-one, ketones, like acetophenone or benzophenone, γ-butyrolactone and ethylene glycols, like Phe-Cellosolve or Bu-Cellosove, or mixtures thereof, in particular mixtures of di- and triarylethers (Dowtherm A®).

It has now surprisingly been found, that the 3,6-diphenyl-furo[3,4-c]pyrrole-1,4-diones (furopyrroles) of formula I can be obtained in higher yield by carrying out the above reaction under microwave radiation. The yield of the ring closure of ethyl 4-benzoyl-4,5-dihydro-5-oxo-2-phenylpyrrole-3-carboxylate to 3,6-diphenylfuro[3,4-c]pyrrole-1,4-dione is, for example, increased from 40 to 86% by the microwave assisted process according to the present invention. Moreover, we have observed that the preparation of this lactone (a versatile DPP precursor) requires lesser time (1 to 10 minutes) under microwave irradiation while ring closure of the compound of formula II takes 60 hours when conducted without microwave radiation (conventional method). In addition, the solvent can be omitted in the microwave assisted ring closure, which makes the above process further cost effective.

Accordingly, the present invention relates to a process for the preparation of furopyrroles of the general formula

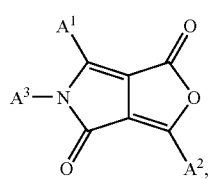

(I)

comprising
(a) heating a compound of the formula

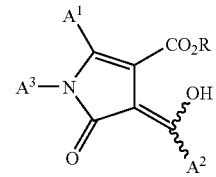

(II)

under microwave irradiation optionally in the presence of an inert solvent,
wherein $A^1$ and $A^2$ are $C_1$-$C_{18}$alkyl, $C_2$-$C_{18}$alkenyl, $C_2$-$C_{18}$alkynyl, $C_5$-$C_8$cycloalkyl, $C_5$-$C_8$cycloalkenyl, aryl or heteroaryl,
$A^3$ is hydrogen, $C_1$-$C_{18}$alkyl, cyanomethyl, $Ar^3$, $-CR^{30}R^{31}-(CH_2)_m-Ar^3$ or $Y-R^{32}$, wherein $R^{30}$ and $R^{31}$ independently of each other stand for hydrogen or $C_1$-$C_4$alkyl, or phenyl which can be substituted up to three times with $C_1$-$C_4$alkyl,
$Ar^3$ stands for aryl, $C_5$-$C_8$cycloalkyl, $C_5$-$C_8$cycloalkenyl or heteroaryl, which can be substituted one to three times with $C_1$-$C_8$alkyl, $C_1$-$C_8$alkoxy, halogen or phenyl, which can be substituted with $C_1$-$C_8$alkyl or $C_1$-$C_8$alkoxy one to three times, and m stands for 0, 1, 2, 3 or 4,
R is $C_1$-$C_{18}$alkyl, in particular $C_1$-$C_4$alkyl, aryl, in particular phenyl, or aralkyl, in particular benzyl, which can be substituted one to three times with $C_1$-$C_8$alkyl, $C_1$-$C_8$alkoxy, or halogen,
Y is $-C(O)-$, $-C(O)O-$, $C(O)NH-$, $-SO_2NH-$ or $-SO_2-$ and
$R^{32}$ is $C_1$-$C_{18}$alkyl, $Ar^3$, or aralkyl.

If desired, the process of the present invention can be carried out in the presence of an inert solvent. Examples of inert solvents include, but are not limited to, aromatic solvents, like biphenyl, para-, meta or ortho-terphenyl, dibenzyltoluene, α-methyl- or β-methylnaphthalene, cyclic carbonates, like 1,3dioxolan-2-one, ketones, like acetophenone or benzophenone, γ-butyrolactone and ethylene glycols, like Phe-Cellosolve or Bu-Cellosove, or mixtures thereof, in particular mixtures of di- and triarylethers (Dowtherm A®).

In a preferred embodiment the compound of the formula II is heated for about 1 to 60 minutes at a temperature of 180 to 280° C., preferably 180-230° C., with or without solvent, under microwave irradiation.

A microwave furnace suitable for the irradiating the composition comprises a microwave source, microwave frequency range selector, a microwave frequency modulator to modulate the microwave frequency across the selected frequency range, microwave forward power controller to select the forward power setting, a thermocouple, an infrared temperature sensor or other temperature measuring means, and a microwave forward power on/off controller to turn the forward power on and off in response to the temperature of the composition. Frequency modulation increases the uniformity of the power distribution throughout the furnace cavity, thereby heating the composition uniformly. Suitable microwave furnaces are described in, for example, U.S. Pat. Nos. 5,321,222 and 5,961,871 to Bible et al., U.S. Pat. No. 5,648,038 to Fathi et al., and U.S. Pat. No. 5,521,360 to Johnson et al. A presently preferred microwave furnace is commercially available from CEM, Inc., as model Discover®. The Discover® System incorporates temperature and pressure feedback systems, for example, an infrared temperature sensor positioned below the reaction vessel, for complete control of the reaction.

It is preferred that the reaction mixture be irradiated in a vessel transparent to microwave radiation in the frequency range employed.

The samples, comprising the compounds of formula II and optionally the solvent, are advantageously heated in pressurized tubes, such as, for example, sealed glass tubes, whereby the pressure is allowed to increase up to $25 \cdot 10^5$ Pa. Preferably the pressure is between 1 to $14 \cdot 10^5$ Pa.

The selection of the actual microwave frequency range will depend on the reactants, but will generally be about 0.9 to about 2.45 GHz. Selection of a forward power input will depend on the nature of the reactants. For example, in the synthesis of 3-(p-bromophenyl)-6-phenyl furo[3,4-c]pyrrole-1,4-dione, a preferred forward power level is about 150 to 300 watts. As described in WO03022848 the furopyrroles of formula I can be used as crystal growth regulators and are intermediates in the synthesis of diketopyrrolopyrroles, which can be obtained by reacting a compound of formula I with a primary amine of the formula $A^4$-$NH_2$ (IV), wherein a DPP of formula

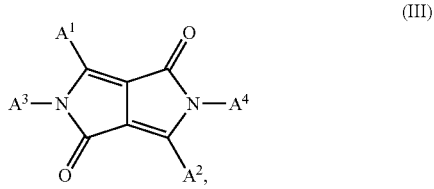

(III)

is obtained, wherein $A^4$ is $C_1$-$C_{18}$alkyl or $Ar^3$, and $A^1$, $A^2$ and $A^3$ are as defined above.

The reaction between the compound of the general formula I and the primary amine or the mixture of primary amines is carried out in a suitable inert solvent or dispersant Suitable solvents or dispersants are, for example, ethers, in particular those having 2 to 8 carbon atoms in the molecule, such as, for example, diethyl ether, methyl ethyl ether, di-n-propyl ether, diisopropyl ether, methyl n-butyl ether, methyl tert-butyl ether, ethyl n-propyl ether, di-n-butyl ether, tetrahydrofuran, 1,4-dioxane, 1,2-dimethoxyethane, bis-β-methoxyethyl ether; oligoethylene glycol dimethyl ethers, such as, for example, pentaglyme; aliphatic hydrocarbons, such as, for example, hexane, heptane, low- and high-boiling petroleum ethers; cycloaliphatic hydrocarbons, such as, for example, cyclohexane, methylcyclohexane, tetralin, decalin; aromatic hydrocarbons, such as, for example, benzene, toluene, o-, m- and p-xylene, ethylbenzene; halogenated aliphatic or aromatic hydrocarbons, such as, for example, methylene chloride, chloroform, carbon tetrachloride, chlorobenzene, dichlorobenzene; nitriles, such as, for example, acetonitrile; amides, such as, for example, dimethylformamide, dimethylacetamide, N-methylpyrrolidone; hexamethylphosphoric triamide; and sulfoxides, such as, for example, dimethyl sulfoxide. Mixtures of various solvents can also be used.

The reaction is preferably carried out in a dipolar or non-polar aprotic solvent. Examples of preferred aprotic solvents are: dimethylformamide, dimethyl sulfoxide, hexamethylphosphoric triamide, sulfolane, N-methylpyrrolidone, tetramethylurea, acetonitrile, ethylene glycol dimethyl ether, ethylene glycol diethyl ether, diethylene glycol dimethyl ether and triethylene glycol dimethyl ether, nitromethane, 1,3-dimethyl-3,4,5,6-tetrahydro-2(1H)-pyrimidinone (DMPU), 1,3dimethyl-2-imidazolidinone, benzonitrile, nitrobenzene, chloroform, carbon tetrachloride and methylene chloride. Particularly preferred aprotic solvents are chloroform, carbon tetrachloride and methylene chloride, of which chloroform is particularly preferred.

The reaction between the compound of the general formula I and the primary amine IV is carried out in the presence of a dehydrating agent. Examples of suitable dehydrating or water-eliminating agents of this type are: N,N'-disubstituted carbodiimides, in particular if they contain at least one secondary or tertiary alkyl radical, such as, for example, diisopropyl-, dicyclohexyl- or N-methyl-N'-tert.-butylcarbodiimide (cf. "The Chemistry of Ketenes, Allenes and Related Compounds", Part 2, Editor: S. Patai, John Wiley & Sons 1980, 722-753). Dicyclohexylcarbodiimide is particularly suitable.

The reaction between the compound of the formula I and the primary amine IV can be carried out, for example, at temperatures from –10° C. up to the boiling point of the solvent or solvent mixture used. In many cases it is carried out at –10 to 30° C. and preferably at room temperature. 0.9 to 1.4 mol, preferably 1.0 to 1.3 mol of the primary amine IV are in general employed per mole of compound of the general formula I. The reaction can be catalyzed by adding a strong non-aqueous acid such as trifluoroacetic acid.

The primary amines IV are known or can be easily prepared by the methods known for the preparation of these class of compound.

The starting compound of the formula Ia, wherein $A^3$ is different from a hydrogen atom, is obtained by reacting a compound of the formula

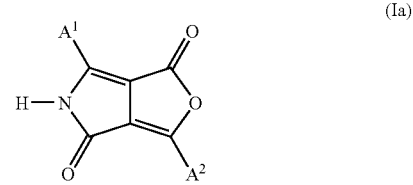

(Ia)

with a compound of the formula $A^3$-X (V), wherein $A^1$, $A^2$ and $A^3$ have the meanings as given above and X is a leaving group. The reaction between the compound of the general formula Ia and the compound of the formula V is carried out in a suitable inert solvent such as tetrahydrofuran, in the presence of a base such as sodium hydride (NaH) or sodium hexamethyidisilazane (NaHMDS), at a temperature ranging from 20° C. to the boiling point of the solvent. The term leaving groups means a group, such as iodo, bromo or chloro, benzene- or p-toluenesulfonate. Processes for the introduction of $A^3$ into compounds of the formula Ia are described, for example, in U.S. Pat. No. 4,585,878.

Suitable alkylating agents are, for example, alkyl halides, in particular alkyl iodides, reactive alkyl esters, in particular alkyl esters of sulfonic acids, such as, for example, alkyl esters of benzene- or p-toluenesulfonic acid. Suitable arylating agents are for example activated aryl compounds such as 1-fluoro-2,4-dinitro-benzene.

The starting compound of the formula IIa is obtained by reacting a compound of the formula

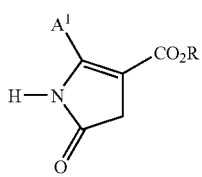

with an ester of the formula $A^2\text{-}CO_2R$ (VII) in the presence of a base, such as for example NaH or NaHMDS at a temperature ranging from 25° C. to the boiling point of the solvent, wherein R, $A^1$ and $A^2$ have the meanings as given above. The starting compounds of the formula VI are known or can be prepared in analogy to processes described in U.S. Pat. Nos. 4,681,971, 4,749,795, 4,720,305 and 4,659,775.

Alternatively, compounds of the formula

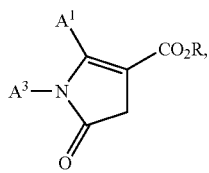

wherein $A^3$ is different from a hydrogen atom and is in particular aryl, can be prepared by a copper catalyzed decomposition of diazoacetates in the presence of enaminoamides (G. Maas, A. Müller, J. prakt. Chem. 340 (1998) 315-322):

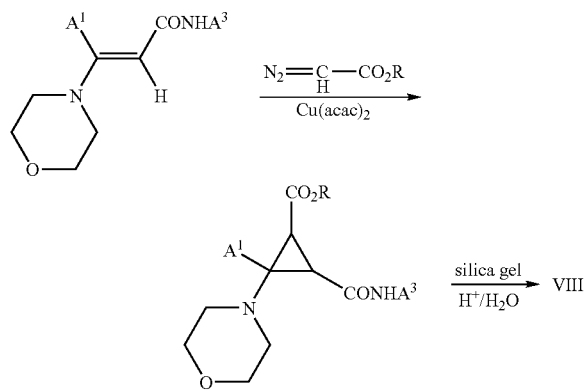

In addition, compounds of formula (VIII) wherein $A^3$ is aryl can be obtained by reacting a compound of formula (IIb) with an amine $A^3\text{-}NH_2$:

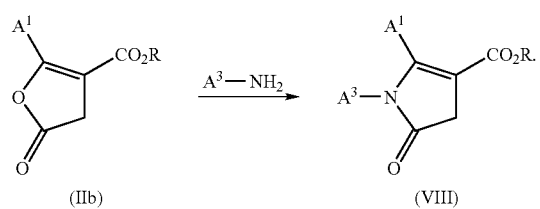

Preferably, the lactone of formula (IIb) is reacted with aniline to afford the N-phenyl pyrrolinone ester of formula (VIII) as described in more detail in Example 4.

The compounds of the formula VI, wherein $A^3$ is different from a hydrogen atom and is in particular aryl, can be reacted to compounds of the formula III as described above.

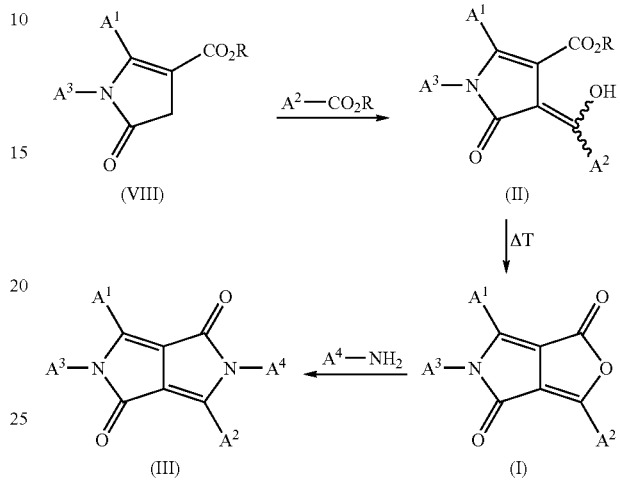

In addition, DPP of formula (III) wherein $A^1$ and $A^2$ are $C_1$-$C_{18}$alkyl, $C_2$-$C_{18}$alkenyl, $C_2$-$C_{18}$alkynyl, $C_5$-$C_8$cycloalkyl, $C_5$-$C_8$cycloalkenyl, aryl or heteroaryl, $A^3$ is hydrogen, $C_1$-$C_{18}$alkyl, cyanomethyl, $Ar^3$, —$CR^{30}R^{31}$—$(CH_2)_m$—$Ar^3$ or Y—$R^{32}$, wherein $R^{30}$ and $R^{31}$ independently of each other stand for hydrogen or $C_1$-$C_4$alkyl, or phenyl which can be substituted up to three times with $C_1$-$C_4$alkyl, $Ar^3$ stands for aryl, $C_5$-$C_8$cycloalkyl, $C_5$-$C_8$cycloalkenyl or heteroaryl, which can be substituted one to three times with $C_1$-$C_8$alkyl, $C_1$-$C_8$alkoxy, halogen or phenyl, which can be substituted with $C_1$-$C_8$alkyl or $C_1$-$C_8$alkoxy one to three times, and m stands for 0, 1, 2, 3 or 4, R is $C_1$-$C_{18}$alkyl, in particular $C_1$-$C_4$alkyl, aryl, in particular phenyl, or aralkyl, in particular benzyl, which can be substituted one to three times with $C_1$-$C_8$alkyl, $C_1$-$C_8$alkoxy, or halogen, Y is —C(O)—, —C(O)O—, —C(O)NH—, —$SO_2$NH— or —$SO_2$—, $R^{32}$ is $C_1$-$C_{18}$alkyl, $Ar^3$, or aralkyl, and $A^4$ is hydrogen can also directly be obtained by reacting a compound of formula (VIII) with a nitrile $A^2$-CN, wherein $A^1$, $A^2$ and $A^3$ have the meanings as given above:

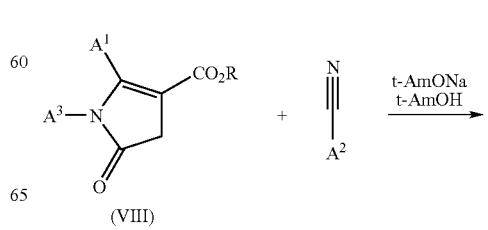

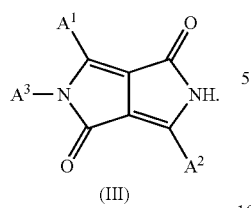

(III)

Further, the compound of the formula III can be reacted with a compound of the formula $A^5$-X, wherein $A^5$ has the meaning of $A^3$ as given above and X is a leaving group. The reaction between these compounds is carried out in a suitable inert solvent such as tetrahydrofuran, in the presence of a base such as sodium hydride (NaH) or sodium hexamethyidisilazane (NaHMDS), at a temperature ranging from 20° C. to the boiling point of the solvent. The term "leaving group" means a group, such as iodo, bromo or chloro, benzene- or p-toluenesulfonate.

Suitable alkylating agents are, for example, alkyl halides, in particular alkyl iodides, reactive alkyl esters, in particular alkyl esters of sulfonic acids, such as, for example, alkyl esters of benzene- or p-toluenesulfonic acid. Suitable arylating agents are for example activated aryl compounds such as 1-fluoro-2,4-dinitro-benzene.

One preferred embodiment concerns DPPs of general formula III wherein residues $A^1$ and $A^2$ are different from phenyl.

The DPPs of the general formula III show a high heat stability, a good solubility in polymers, hydrocarbon based fuels, lubricants, and water, a high light stability, and the ability to be used in plastics, especially polyamides, without decomposition and loss of lightfastness, and in paints; and can show photo- and electroluminescence as well as solid state fluorescence. The residues $A^1$ and $A^2$ are in general selected from $C_1$-$C_{18}$alkyl, $C_2$-$C_{18}$alkenyl, $C_2$-$C_{18}$alkynyl, $C_5$-$C_8$cycloalkyl, such as cyclopentyl, cyclohexyl, cycloheptyl and cyclooctyl, in particular cyclohexyl, $C_5$-$C_8$cycloalkenyl, such as cyclopentenyl, cyclopentadienyl and cyclohexenyl, in particular cyclohex3-enyl, aryl and heteroaryl.

Diketopyrrolopyrroles, wherein $A^1$ and $A^2$ are radicals of the formula

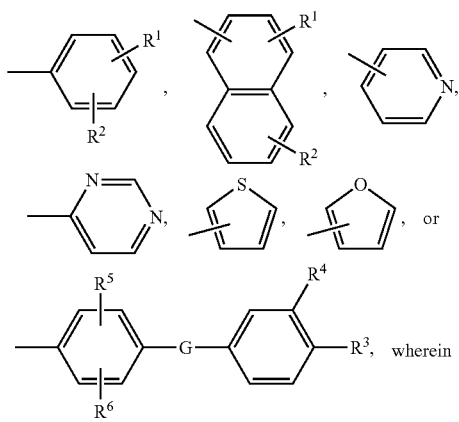

wherein $R^1$ and $R^2$ are independently of each other hydrogen, halogen, $C_1$-$C_{18}$alkyl, $C_1$-$C_{18}$alkoxy, $C_1$-$C_{18}$alkylmercapto, di($C_1$-$C_{18}$alkyl)amino, $C_1$-$C_{18}$alkylamino, $C_1$-$C_{18}$alkoxycarbonyl, $C_1$-$C_{18}$alkylaminocarbonyl, —CN, —$NO_2$, trifluoromethyl, $C_5$-$C_8$cycloalkyl, —C=N—($C_1$-$C_{18}$alkyl), phenyl,

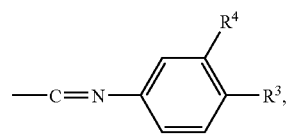

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, —$CONX^5X^6$, —$C(O)OX^7$ or —$SO_2X^9$; wherein $X^5$ and $X^6$ are hydrogen, linear or branched $C_{1-10}$-alkyl, $C_{5-10}$cycloalkyl or $C_{6-10}$-aryl, $X^7$ is hydrogen, linear or branched $C_{1-10}$-alkyl, $C_{5-10}$-cycloalkyl or $C_{6-10}$-aryl, $X^9$ is hydrogen, linear or branched $C_{1-10}$-alkyl, $C_{5-10}$-cycloalkyl, $C_{7-10}$-aralkyl, $C_{6-10}$-aryl or —$NX^{10}X^{11}$, wherein $X^{10}$ and $X^{11}$ are hydrogen, linear or branched $C_{1-10}$-alkyl, $C_{7-10}$-aralkyl or $C_{6-10}$-aryl, G is —$CH_2$—, —$CH(CH_3)$—, —$C(CH_3)_2$—, —CH=N—, —N=N—, —O—, —S—, —SO—, —$SO_2$—, —CONH— or —$NR^7$—, $R^3$ and $R^4$ are independently of each other hydrogen, halogen, $C_1$-$C_6$alkyl, $C_1$-$C_{18}$alkoxy or —CN, $R^5$ and $R^6$ are independently of each other hydrogen, halogen or $C_1$-$C_6$alkyl, and $R^7$ is hydrogen or $C_1$-$C_6$alkyl are preferred, wherein radicals of the formula

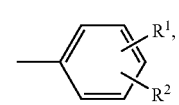

wherein $R^1$ and $R^2$ are independently of each other hydrogen, chloro, bromo, $C_1$-$C_4$alkyl, $C_1$-$C_6$alkoxy, $C_1$-$C_6$alkylamino, phenyl or CN, G is —O—, —$NR^7$—, —N=N— or —$SO_2$—, $R^3$ and $R^4$ are hydrogen, and $R^7$ is hydrogen, methyl or ethyl are further preferred and diketopyrrolopyrrole analogues, wherein $A^1$ and $A^2$ are radicals of the formula wherein $R^1$ and $R^2$ are independently of each other hydrogen, methyl, tert-butyl, chloro, bromo, phenyl or CN are particularly preferred for the preparation of inks, colorants, pigmented plastics for coatings, non-impact-printing material, color filters, cosmetics, polymeric ink particles, toners.

In the case of electroluminescence applications the following residues are preferred for $A^1$ and $A^2$:

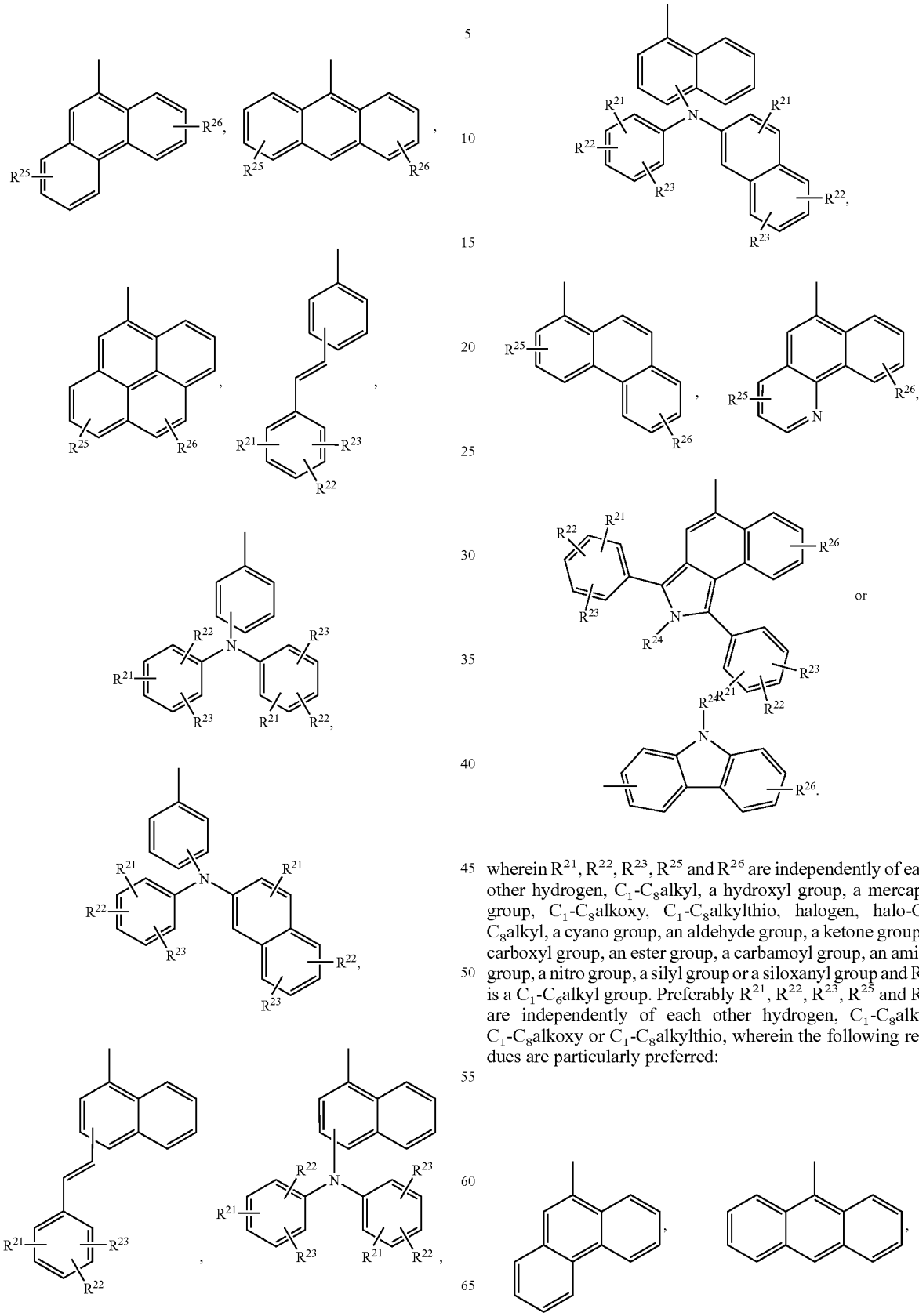

wherein $R^{21}$, $R^{22}$, $R^{23}$, $R^{25}$ and $R^{26}$ are independently of each other hydrogen, $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group and $R^{24}$ is a $C_1$-$C_6$alkyl group. Preferably $R^{21}$, $R^{22}$, $R^{23}$, $R^{25}$ and $R^{26}$ are independently of each other hydrogen, $C_1$-$C_8$alkyl, $C_1$-$C_8$alkoxy or $C_1$-$C_8$alkylthio, wherein the following residues are particularly preferred:

-continued

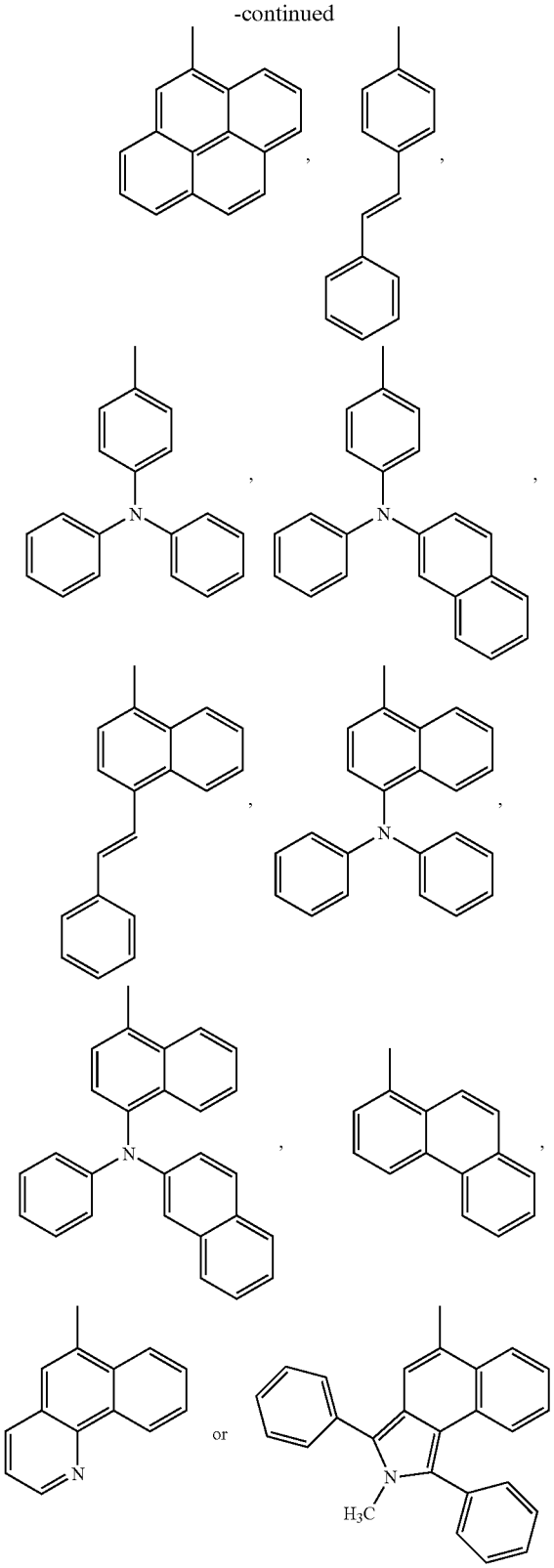

The residue $A^3$ is in general selected from hydrogen, $C_1$-$C_{18}$alkyl, cyanomethyl, $Ar_3$, —$CR^{30}R^{31}$—$(CH_2)_m$—$Ar^3$ or Y—$R^{32}$, wherein $R^{30}$ and $R^{31}$ independently of each other stand for hydrogen or $C_1$-$C_4$alkyl, or phenyl which can be substituted up to three times with $C_1$-$C_3$alkyl, $Ar^3$ stands for aryl, in particular phenyl or 1- or 2-naphthyl, $C_5$-$C_8$cycloalkyl, such as cyclopentyl, cyclohexyl, cycloheptyl and cyclooctyl, in particular cyclohexyl, $C_5$-$C_8$cycloalkenyl, in particular cyclopentenyl, cyclopentadienyl and cyclohexenyl, or heteroaryl, which can be substituted one to three times with $C_1$-$C_8$alkyl, $C_1$-$C_8$alkoxy, halogen or phenyl, which can be substituted with $C_1$-$C_8$alkyl or $C_1$-$C_8$alkoxy one to three times, and m stands for 0, 1, 2, 3 or 4, Y is —C(O)—, —C(O)O—, —C(O)NH—, —SO$_2$NH— or —SO$_2$— and $R^{32}$ is $C_1$-$C_{18}$alkyl, $Ar^3$, or aralkyl.

$A^3$ is preferably hydrogen, $C_1$-$C_8$alkyl such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, Y—$R^{32}$ wherein Y is —C(O)— and $R^{32}$ is

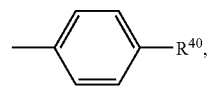

wherein $R^{40}$ is $C_1$-$C_4$alkyl, —O—$C_1$-$C_4$alkyl, or —S—$C_1$-$C_4$alkyl and —$(CH_2)_m$—Ar wherein m is 1 and Ar is a group of the formula

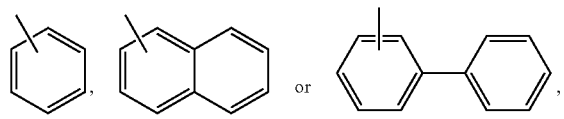

which can be substituted one to three times with $C_1$-$C_8$alkyl, $C_1$-$C_8$alkoxy, halogen or phenyl.
Examples of preferred residues Ar are

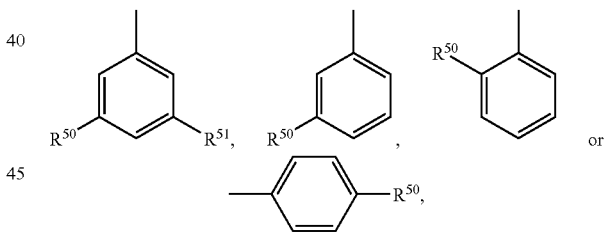

wherein $R^{50}$ and $R^{51}$ are independently of each other methyl, ethyl, n-propyl, isopropyl, n-butyl, sec.-butyl, isobutyl, tert.-butyl, methoxy, ethoxy, isopropoxy, tert.-butoxy or chlorine.

The residue $A^4$ is in general selected from $C_1$-$C_{18}$alkyl or $Ar^3$, in particular $Ar^3$, wherein $A^4$ is preferably

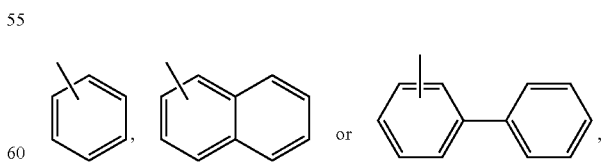

which can be substituted one to three times with $C_1$-$C_8$alkyl, $C_1$-$C_8$alkoxy, halogen or phenyl.

The furopyrroles of the formula I are intermediates in the process for the preparation of the diketopyrrolopyrroles of the formula III and, as described in WO03022848, can be used as crystal growth regulators, wherein the term "regulating the crystal growth" refers to controlling the synthesis of pigment particles to have a suitable pigmentary size and/or a narrow particle size distribution as well as directing the growth of the crystals to generate particles of a specifically desired shape, such as platelet, needle, cubic, leaflet, prismatic and other geometric forms and/or of a specifically desired rheology. Consequently, the better control of the crystal growth affords samples with a narrower particle size distribution and/or a better crystal shape, or both. The effect can be influenced by the chemical structure of the organic pigment, the selection of the reaction media and the concentration and chemical structure of the inventive particle growth regulator.

If used as crystal growth regulator the furopyrroles of the formula I are present in amount of from about 0.1-20%, especially from 1.0 to 10.0%, based on primary pigment weight. Although DPPs are preferred as primary pigment, the use of diverse pigment moieties is likewise available where the respective pigments are color compatible.

Examples of applicable organic primary pigments are: anthraquinone, phthalocyanine, perinone, perylene, dioxazine, diketopyrrolopyrrole, thioindigo, isoindoline, isoindolinone, quinacridone, quinacridonequinone, flavanthrone, indanthrone, anthrapyrimidine or quinophthalone pigments, and solid solutions comprising these pigments. Preferred organic pigments are quinacridones, phthalocyanines, anthraquinones, perylenes, diketopyrrolopyrroles, isoindolinones and indanthrones.

When the pigment compositions are prepared, the diketopyrrolopyrrole analogues of the formula I can be added during the pigment synthesis, during the fine dispersion process, before or after a finishing process by methods well-known in the art (cf. WO03022848).

Furopyrroles of the formula I, wherein $A^1$ and $A^2$ are radicals of the formula

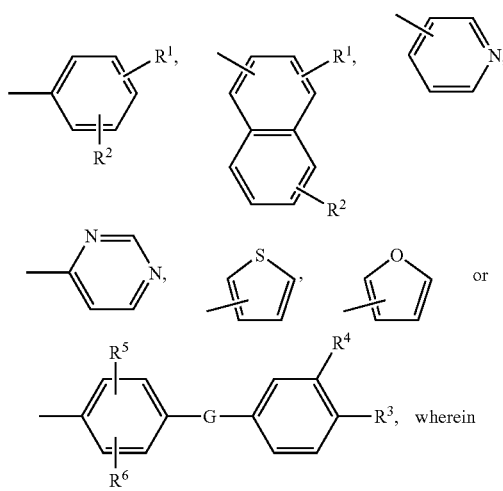

$R^1$ and $R^2$ are independently of each other hydrogen, halogen, $C_1$-$C_{18}$alkyl, $C_1$-$C_{18}$alkoxy, $C_1$-$C_{18}$alkylmercapto, $C_1$-$C_{18}$alkylamino, $C_1$-$C_{18}$alkoxycarbonyl, $C_1$-$C_{18}$alkylaminocarbonyl, —CN, —NO$_2$, trifluoromethyl, $C_5$-$C_8$cycloalkyl, —C=N—($C_1$-$C_{18}$alkyl), phenyl,

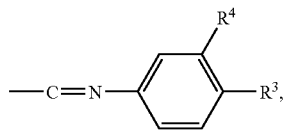

imidazolyl, pyrazolyl, triazolyl, piperazinyl, pyrrolyl, oxazolyl, benzoxazolyl, benzothiazolyl, benzimidazolyl, morpholinyl, piperidinyl or pyrrolidinyl, —CONX$^5$X$^6$, —C(O)OX$^7$, —SX$^9$, —OX$^9$, or —SO$_2$X$^9$; wherein X$^5$ and X$^6$ are hydrogen, linear or branched $C_{1-10}$-alkyl, $C_{5-10}$-cycloalkyl or $C_{6-10}$-aryl, X$^7$ is hydrogen, linear or branched $C_{1-10}$-alkyl, $C_{5-10}$-cycloalkyl or $C_{6-10}$-aryl, X$^9$ is hydrogen, linear or branched $C_{1-18}$-alkyl, $C_{5-10}$-cycloalkyl, $C_{7-10}$-aralkyl, $C_{6-10}$-aryl or —NX$^{10}$X$^{11}$, wherein X$^{10}$ and X$^{11}$ are hydrogen, linear or branched $C_{1-10}$-alkyl, $C_{7-10}$-aralkyl or $C_{6-10}$-aryl, G is —CH$_2$—, —CH(CH$_3$)—, —C(CH$_3$)$_2$—, —CH=N—, —N=N—, —O—, —S—, —SO—, —SO$_2$—, —CONH— or —NR$^7$—, $R^3$ and $R^4$ are independently of each other hydrogen, halogen, $C_1$-$C_6$alkyl, $C_1$-$C_{18}$alkoxy or —CN, R$^5$ and R$^6$ are independently of each other hydrogen, halogen or $C_1$-$C_6$alkyl, and R$^7$ is hydrogen or $C_1$-$C_6$alkyl are preferred, wherein radicals of the formula

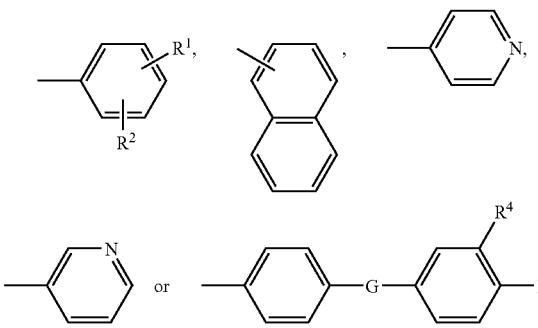

wherein $R^1$ and $R^2$ are independently of each other hydrogen, chloro, bromo, $C_1$-$C_4$alkyl, $C_1$-$C_6$alkoxy, $C_1$-$C_6$alkylamino, phenyl or CN, —CONX$^5$X$^6$, —SX$^9$, —SOX$^9$, or —SO$_2$X$^9$; or —SO$_2$X$^9$; wherein X$^5$ and X$^6$ are hydrogen, linear or branched $C_{1-4}$-alkyl, X$^9$ is hydrogen, linear or branched $C_{1-18}$-alkyl, $C_{7-10}$-aralkyl, $C_{6-10}$-aryl or —NX$^{10}$X$^{11}$, wherein X$^{10}$ and X$^{11}$ are hydrogen, linear or branched $C_{1-10}$-alkyl, $C_{7-10}$-aralkyl or $C_{6-10}$-aryl;

G is —O—, —NR$^7$—, —N=N—, —S—, —SO— or —SO$_2$—, $R^3$ and $R^4$ are hydrogen, and $R^7$ is hydrogen, methyl or ethyl are further preferred and diketopyrrolopyrrole analogues, wherein $A^1$ and $A^2$ are radicals of the formula

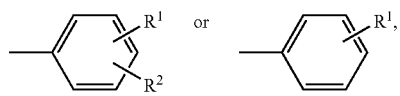

wherein $R^1$ and $R^2$ are independently of each other hydrogen, $C_{1-4}$alkyl, such as methyl or tert-butyl, halogen, such as chloro or bromo, $C_{1-4}$alkoxy or $C_{1-4}$-thioalkyl, phenyl or CN or —SO$_2$X$^9$, wherein X$^9$ is $C_{1-4}$alkyl, phenyl, benzyl or $NX^{10}X^{11}$, wherein $X^{10}$ and $X^{11}$ are hydrogen, $C_{1-4}$-alkyl, benzyl or phenyl are particularly preferred.

$A^3$ is preferably hydrogen, $C_1$-$C_8$alkyl such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, Y—$R^{32}$ wherein Y is —C(O)— and $R^{32}$ is

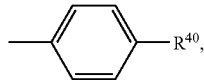

wherein $R^{40}$ is $C_1$-$C_4$alkyl, —O—$C_1$-$C_4$alkyl, or —S—$C_1$-$C_4$alkyl and —$CH_2$)$_m$—Ar wherein m is 1 and Ar is a group of the formula

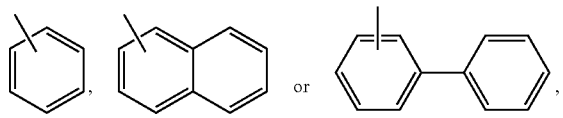

which can be substituted one to three times with $C_1$-$C_8$alkyl, $C_1$-$C_8$alkoxy, halogen or phenyl.

$C_1$-$C_{18}$alkyl is typically linear or branched—where possible—and examples of $C_1$-$C_{18}$alkyl are methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, n-nonyl, decyl, undecyl, dodecyl, tetradecyl, pentadecyl, hexadecyl, heptadecyl and octadecyl. $C_1$-$C_8$alkyl such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl is preferred. $C_1$-$C_4$alkyl such as methyl, ethyl, n-propyl, isopropyl, n-butyl, sec.-butyl, isobutyl or tert.-butyl is particularly preferred. The term "$C_2$-$C_{18}$alkenyl group" means an unsaturated linear or branched aliphatic hydrocarbon group containing one or more double bonds, in particular $C_{2-8}$-alkenyl, such as vinyl, allyl, 2-propen-2-yl, 2-buten-1-yl, 3-buten-1-yl, 1,3-butadien-2-yl, 2-penten-1-yl, 3-penten-2yl, 2-methyl-1-buten-3-yl, 2-methyl-3-buten-2-yl, 3-methyl-2-buten-1-yl and 1,4-pentadien-3-yl. The term "$C_2$-$C_8$alkynyl group" means an unsaturated aliphatic hydrocarbon group containing a triple bond, in particular $C_2$-$C_8$-alkynyl such as ethynyl, 1-propyn-1-yl, 2-butyn-1-yl, 3-butyn-1-yl, 2-pentyn-1-yl and 3-pentyn-2-yl.

Examples of $C_1$-$C_{18}$alkoxy, which can be linear or branched, are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, wherein $C_1$-$C_4$alkoxy such as methoxy, ethoxy, n-propoxy, isopropoxy, n-butoxy, sec.-butoxy, isobutoxy and tert.-butoxy is preferred. Examples of $C_1$-$C_{18}$alkylmercapto are the same groups as mentioned for the alkoxy groups, except that the oxygen atom of the ether linkage is replaced by a sulphur atom. Examples and preferences for $C_1$-$C_{18}$alkyl in $C_1$-$C_{18}$alkylamino and $C_1$-$C_{18}$alkylaminocarbonyl are the same as mentioned for $C_1$-$C_{18}$alkyl. Examples and preferences for $C_1$-$C_{18}$alkoxy in $C_1$-$C_{18}$alkoxycarbonyl are the same as mentioned for $C_1$-$C_{18}$alkoxy.

The term "aryl group" is typically $C_6$-$C_{24}$aryl, such as phenyl, 1-naphthyl, 2-naphthyl, 4-biphenyl, phenanthryl, terphenyl, pyrenyl, 2- or 9-fluorenyl or anthracenyl, preferably $C_6$-$C_{12}$aryl such as phenyl, 1-naphthyl, 2-naphthyl, 4biphenyl, which may be unsubstituted or substituted.

The term "aralkyl group" is typically $C_7$-$C_{24}$aralkyl, such as benzyl, 2-benzyl-2-propyl, β-phenylethyl, α,α-dimethylbenzyl, ω-phenylbutyl, ω,ω-dimethyl-ω-phenylbutyl, ω-phenyldodecyl, ω-phenyloctadecyl, ω-phenyleicosyl or ω-phenyidocosyl, preferably $C_7$-$C_{18}$aralkyl such as benzyl, 2-benzyl-2-propyl, β-phenylethyl, α,α-dimethylbenzyl, ω-phenylbutyl, ω,ω-dimethyl-ω-phenylbutyl, ω-phenyldodecyl or ω-phenyloctadecyl, and particularly preferred $C_7$-$C_{12}$aralkyl such as benzyl, 2-benzyl-2-propyl, β-phenylethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted.

Examples of $C_5$-$C_8$cycloalkyl are cyclopentyl, cyclohexyl, cycloheptyl and cyclooctyl, which may be unsubstituted or substituted. The term "$C_5$-$C_8$cycloalkenyl group" means an unsaturated alicyclic hydrocarbon group containing one or more double bonds, such as cyclopentenyl, cyclopentadienyl and cyclohexenyl, which may be unsubstituted or substituted.

The term "heteroaryl" is a ring with five to seven ring atoms, wherein nitrogen, oxygen or sulfur are the possible hetero atoms, and is typically an unsaturated heterocydic radical with five to 18 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl.

Examples of a halogen atom are fluorine, chlorine, bromine and iodine.

If the above-mentioned substituents can be substituted, possible substituents are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group.

As described in WO03022848 the DPPs of the general formula III can be used for the preparation of inks for printing inks in printing processes, for flexographic printing, screen printing, packaging printing, security ink printing, intaglio printing or offset printing, for pre-press stages and for textile printing, for office, home applications or graphics applications, such as for paper goods, for example, for ballpoint pens, felt tips, fiber tips, card, wood, (wood) stains, metal, inking pads or inks for impact printing processes (with impact-pressure ink ribbons), for the preparation of colorants for coating materials, for industrial or commercial use, for textile decoration and industrial marking, for roller coatings or powder coatings or for automotive finishes, for high-solids (low-solvent), water-containing or metallic coating materials or for pigmented formulations for aqueous paints, for the preparation of pigmented plastics for coatings, fibers, platters or mold carriers, for the preparation of non-impact-printing material for digital printing, for the thermal wax transfer printing process, the ink jet printing process or for the thermal transfer printing process, and also for the preparation of color filters, especially for visible light in the range from 400 to 700 nm, for liquid-crystal displays (LCDS) or charge combined devices (CCDs) or for the preparation of cosmetics or for the preparation of polymeric ink partides, toners, dye lasers, dry copy toners liquid copy toners, or electrophotographic toners, and electroluminescent devices.

The following examples illustrate various embodiments of the invention, but the scope of the invention is not limited thereto.

The microwave generator used was a CEM Discover® model, with a circular single mode cavity design, that focuses the microwave radiation on the sample. The sample was contained in a sealed glass tube, whereby the pressure was allowed to increase to a maximum of $20.69 \cdot 10^5$ Pa (300 p.s.i.). The maximum operating power of this device was 300 watts. $^1$H and $^{13}$C NMR spectra were obtained at 300 and 75 MHz respectively, and coupling constants are in Hz. Mass spectral measurements were obtained using chemical ionisation at 70 eV, with isobutane as carrier gas.

EXAMPLES

Example 1

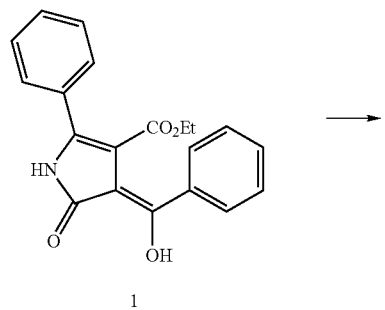

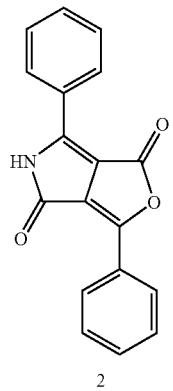

3,6-Diphenylfuro[3,4-c]pyrrole-1,4-dione (2)

Ethyl 4-benzoyl-4,5-dihydron-5-oxo-2-phenylpyrrole-3-carboxylate 1 (99.5 mg, 0.296 mmol, prepared as previously reported in WO03022848) was irradiated with microwave radiation (at a frequency of 2 to 45 GHz, and a forward power of 300 Watts) without solvent, heating to 250° C. for 10 minutes. The crude product was then allowed to cool, methanol was added and the solid filtered off and washed with methanol. This gave the furopyrrole 2 as an orange solid (73 mg, 86%). Decomp>300° C.

$\delta_H$ (DMSO $d_6$) 11.87 (1H, s, NM, 8.12-8.23 (4H, dm, Ar—H) and 7.48-7.54 (6H, m, Ar—H);

$\delta_C$ (DMSO $d_6$) 161.4, 159.3 (2×C=O), 152.2, 148.1 (2×quat.), 132.8, 132.6, 129.1 (2C), 128.0, 127.0 (6×Ar C—H), 126.8, 126.4, 115.8, 102.8(4×quat.).

Comparative Example 1 (Example 1 of WO03022848)

A mixture of ethyl 4-benzoyl-4,5-dihydro-5-oxo-2-phenylpyrrole-3-carboxylate 1 (10 g, 0.0299 mol) and Dowtherm A (200 ml) was heated to 230-240° C. under nitrogen for 64 h. The solution was then cooled to 25° C. and added dropwise to petrol ether 40-60 (300 ml) upon which a fluorescent orange solid precipitated. This was filtered off, washed with further hexane and dried in vacuo. Yield 3.48 g (40%).

Example 2

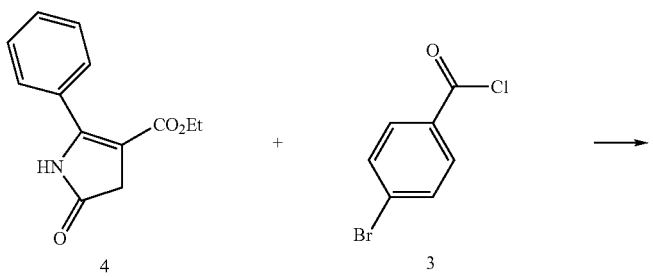

-continued

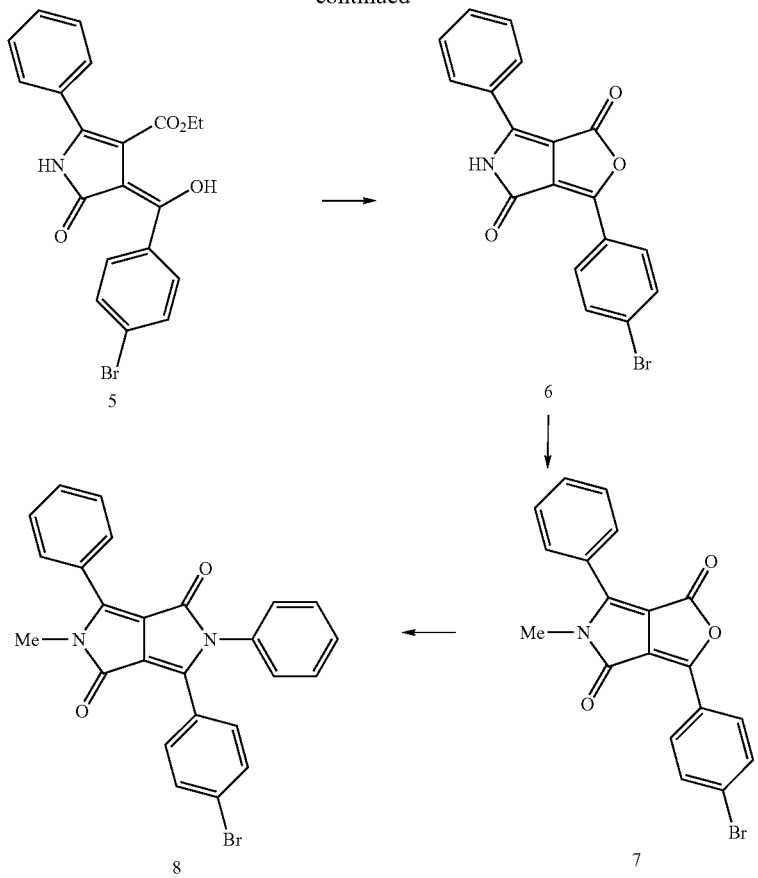

a) p-Bromobenzoyl Chloride (3)

p-Bromobenzoic acid was purified by dissolving in NaOH (aq) and washing the solution with dichloromethane, followed by acidification of the aqueous layer with dilute aqueous HCl, and extraction with EtOAc. The acid (4.00 g, 0.0182 mol), oxalyl chloride (4.634 g, 3.185 ml, 0.0364 mol), and a catalytic amount of DMF was stirred overnight at room temperature in DCM (40 ml). Evaporation of the solvents and excess reagents gave the acid chloride 3 as an off-white solid. m.p. 38-40° C.

b) Ethyl 4-(p-bromobenzoyl)-4,5-dihydro-5-oxo-2-phenylpyrrole-3-carboxylate (5)

To sodium hydride (590 mg, 14.75 mmol) was added THF (40 ml), and the pyrrolinone ester 4 (852 mg, 3.69 mmol). After stirring for 30 mins at room temperature, a solution of p-bromobenzoyl chloride (809.5 mg, 3.69 mmol) in THF (10 ml) and a catalytic amount of DMAP, was added and the mixture was stirred at room temperature overnight. 10% HCl (aq) was added, and the organic component extracted with diethyl ether. Concentration in vacuo and recrystallisation from ethanol gave the enol 5 as a yellow crystalline solid (665 mg, 44%). M.p. 189° C.; $\delta_H$ (DMSO d-$_6$) 11.90 (1H, s, NH), 7.72-7.82 (2H, m, ArH), 7.58-7.66 (4H, m, ArH), 7.42-7.53 (3H, m, ArH), 3.72 (2H, q, $CH_2CH_3$) and 0.9 (3H, t, $CH_2CH_3$); m/z 416 (M+1 $^{81}$Br, 100%), 414 (M+1 $^{79}$Br, 96%) 347, 319, 317, 296 c) 3-(p-Bromophenyl)-6-phenyl furo[3,4-c]pyrrole-1,4-dione (6)

The p-bromobenzoylpyrrolinone ester 5 (154 mg, 0.37 mmol) was irradiated with microwave radiation (at a frequency of 2 to 45 GHz, and a forward power of 300 Watts) without solvent, heating to 250° C. for 10 minutes. The crude product was then allowed to cool, methanol was added and the solid filtered off and washed with methanol. This gave the furopyrrole 6 as a red solid (129 mg, 94%). M.p. 295° C. (subl., decomp.); $\delta_H$ (DMSO d$_6$) 11.88 (1H, s, NH), 8.13-8.17 (2H, m, Ar—H), 7.98 and 7.66 (2×2H, AA'BB', J 8.7, $C_6H_4$) and 7.43-7.47 (3H, m, Ar—H); m/z 370 (M+1 $^{81}$Br, 94%) and 368 (M+1 $^{79}$Br, 100%).

d) 5-Methyl-3-(p-bromophenyl)-6-phenylfuro[3,4-c]pyrrole-1,4-dione (7)

A mixture of furopyrrole 6 (1.5 g, 4.08 mmol), methyl tosylate (1.14 g, 6.12 mmol), potassium carbonate (1.13 g, 8.16 mmol) and dimethylformamide was stirred at room temperature overnight. Water was then added, and the organic component extracted with DCM. The solvent was removed, and washing with water then methanol gave the methylated compound 7 as a red solid (0.831 g, 53%), m.p. 215-216° C. $\delta_H$ (CDCl$_3$) 8.19 and 7.61 (each 2H, AA'BB', p-C$_6$H$_4$Br), 7.78-7.73 (2H, m, o-Ph), 7.54-7.50 (3H, m, m/p-Ph) and 3.38 (3H, s, NCH$_3$). $\lambda_{max}$ (abs) (DCM)/nm 454 ($\epsilon$ 15,878)

e) 2-Methyl-5-phenyl-6-(p-Bromophenyl)-3-phenylpyrrolo[3,4-c]pyrrole-1,4-dione (8)

A mixture of furopyrrole 7 (300 mg, 0.79 mmol), aniline (146 mg, 1.57 mmol), DCC (323 mg, 1.57 mmol), trifluoroacetic acid (2-3 drops) and DCM was stirred at room temperature for 144 hours. The solvent was removed, and washing with methanol gave the pyrrolopyrrole 8 as a red solid (173 mg, 55%), m.p. 255-256° C. $\delta_H$(CDCl$_3$) 7.88-7.83 (2H, m, Ar—H), 7.49-7.43 (5H, m, Ar—H), 7.40-7.26 (5H, m, Ar—H), 7.12-7.07 (2H, m, Ar—H) and 3.35 (3H, s, NCH$_3$)

Example 3 a) Ethyl 4-(p-nitrobenzoyl)-4,5-dihydro-5-oxo-2-phenylpyrrole-3-carboxylate (11)

The pyrrolinone ester 9 (6.35 g, 27.5 mmol) was added to a mixture of sodium hydride (2.0 g, 82.5 mmol) and THF (1 litre), and this was stirred at room temperature for 15 minutes. p-Nitrobenzoyl chloride 10 was then added, and the mixture was stirred overnight. Methanol was added, followed by water and the mixture acidified with HCl. The organic component was extracted with diethyl ether and the solvent evaporated. Washing with methanol gave the nitro compound 11 as a yellow solid (6.31 g, 60%). $\delta_H$(DMSO-d$_6$) 11.95 (1H, s, NH), 8.30 and 7.84 (each 2H, AA'BB', Ar), 7.56-7.50 (2H,

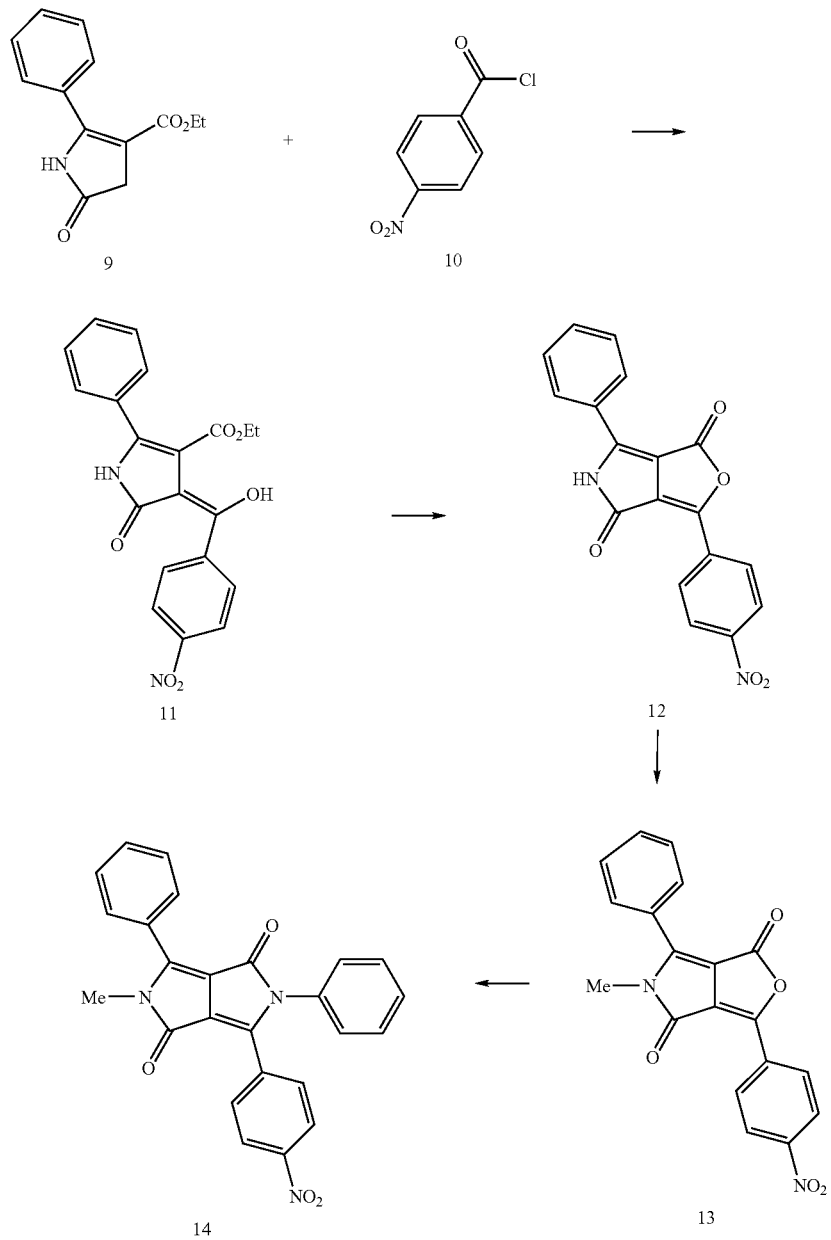

m, o-Ph), 7.45-7.35 (3H, m, m/p-Ph), 3.62 (2H, q, OCH$_2$CH$_3$) and 0.75 (3H, t, OCH$_2$CH$_3$). m/z (ESI-ve) 380 (22%, M$^+$), 379 [100%, (M−1)]$^+$ b) 3-(p-Nitrophenyl)-6-phenylfuro[3,4-c]pyrrole-1,4-dione (12)

The p-nitrobenzoylpyrrolinone ester 11 (300 mg, 0.90 mmol) was irradiated with microwave radiation without solvent, heating to 270° C. for 15 minutes. The crude product was then allowed to cool, methanol was added and the solid filtered off and washed with methanol. This gave the furopyrrole 12 as a red solid (230 mg, 87%).

δ$_H$ (DMSO-d$_6$) 12.15 (1H, s, NH), 8.38 (4H, s, p-C$_6$H$_4$NO$_2$), 8.34-8.28 (2H, m, o-Ph) and 7.69-7.58 (3H, m, m/p-Ph). m/z (ESI-ve) 334 (21%, M$^+$), 333 [100%, (M−1)]$^+$ c) 5-Methyl-3-(p-nitrophenyl)-6-phenylfuro[3,4-c]pyrrole-1,4-dione (13)

A mixture of furopyrrole 12 (0.9 g, 2.7 mmol), methyl tosylate (750 mg, 4.04 mmol), potassium carbonate (1 g, 7.2 mmol) and dimethyl formamide was stirred at room temperature overnight. Water was then added, and the organic component extracted with DCM. The solvent was removed, and washing with water then methanol gave the methylated compound 13 as a red solid (0.652 g, 70%), m.p. 253-255° C. δ$_H$ (CDCl$_3$) 8.55 and 8.38 (4H, AA'BB', Ar), 7.88-7.84 (2H, m, o-Ph), 7.65-7.60 (3H, m, m/p-Ph) and 3.49 (3H, s, NCH$_3$). λ$_{max}$ (abs) (DCM)/nm 482 (ε 17,462)

d) 2-Methyl-5'-phenyl-6-(p-nitrophenyl)-3-phenylpyrrolo[3,4-c]pyrrole-1,4-dione (14)

A mixture of furopyrrole 13 (100 mg, 0.29 mmol), aniline (53 mg, 0.57 mmol), DCC (118 mg, 0.57 mmol), trifluoroacetic acid (2-3 drops) and DCM was stirred at room temperature for 72 hours. The solvent was removed, and washing with methanol gave the pyrrolopyrrole 14 as a red solid (63 mg, 52%), m.p. 233-235° C. δ$_H$ (CDCl$_3$) 8.16 and 7.81 (each 2H, AA'BB', p-C$_8$H$_4$NO$_2$), 7.98-7.93 (2H, m, o-Ph), 7.60-7.55 (3H, m, m/p-Ph), 7.44-7.36 (3H, m, m/p-Ph), 7.20-7.15 (2H, m, o-Ph) and 3.45 (3H, s, NCH$_3$). α$_{max}$ (abs) (DCM)/nm 493 (ε 14,014)

Example 4

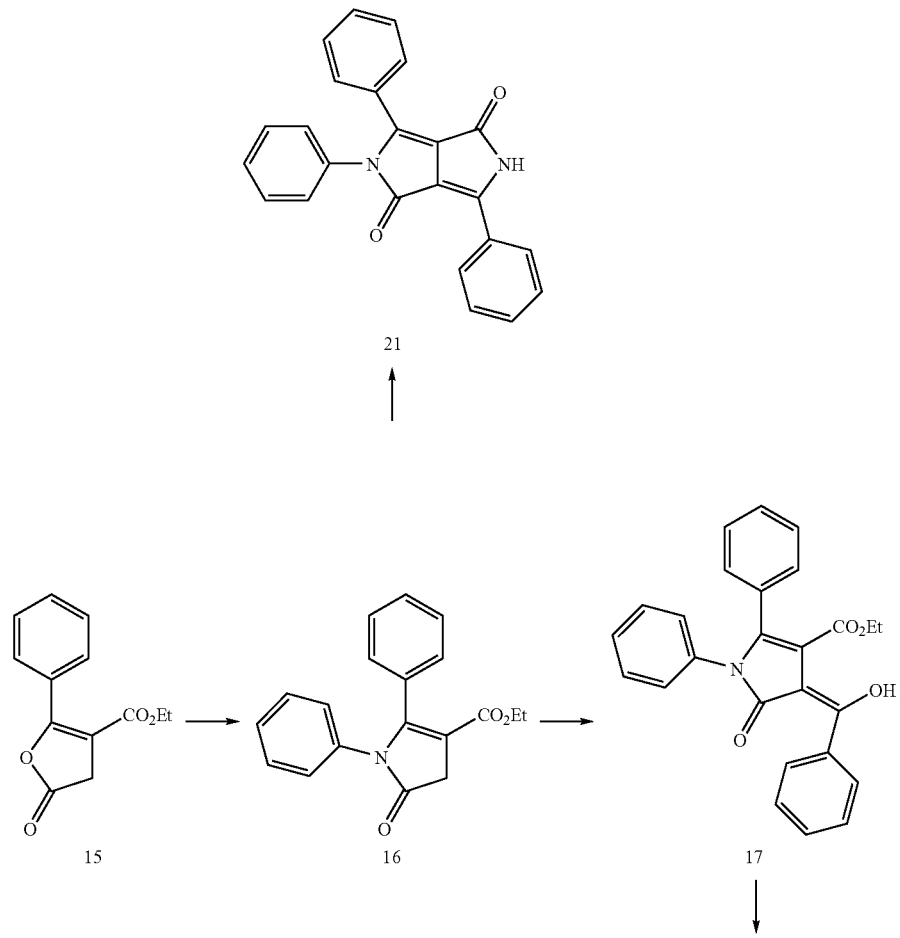

-continued

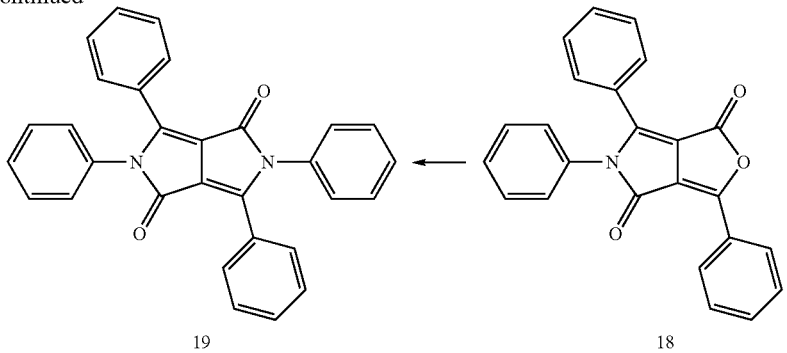

19    18 a) Ethyl 4,5-dihydro-5-oxo-1,2-diphenylprrole-3-carboxylate (16)

Aniline (2.65 g, 2.59 ml, 0.0285 mmol) was added to a solution of ethyl 5-oxo-2-phenyl4,5-dihydro-furan-3-carboxylate 15 (made via the literature method described in F. Gaudemar-Bardone, M. Mladenova, R. Couffignal, *Synthesis*, 1985, 1043) (6.0 g, 0.0259 mmol) and acetic acid (100 ml), and the solution heated to relux for 3 hours. The solution was then cooled, diluted with water and extracted with diethyl ether. The organic extracts were dried and concentrated. Column chromatography (silica gel, eluent dichloromethane) gave the lactam 16 as a colourless solid (6.9 g, 87% ), m.p. 129-130° C. $\delta_H$ (CDCl$_3$) 7.32-7.15 (8H, m, Ar—H), 6.98-6.93 (2H, m, o-Ph-N), 4.08 (2H, q, OCH$_2$CH$_3$, J 6.9), 3.67 (2H, s, CH$_2$) and 1.11 (3H, t, OCH$_2$CH$_3$, J 6.9)

b) Ethyl 4-benzoyl-4,5-dihydro-5-oxo-1,2-diphenylpyrrole-3-carboxylate (17)

A solution of pyrrolinone ester 16 (1.76 g, 5.74 mmol) in tetrahydrofuran (100 ml) was cooled to −78° C., and a 1.0 M solution of lithium hexamethyidisilazide (17.2 ml, 17.2 mmol) in THF was added. After 5 minutes, benzoyl chloride (0.97 g, 0.79 ml, 6.89 mmol) was added, and the solution stirred for 30 mins. Methanol was added, and the solution warmed to room temperature. The mixture was acidified (aqueous HCl) and extracted with diethyl ether. The ether extracts were dried and concentrated. Column chromatography (silica gel, eluent dichloromethane) gave the enol 17 as a yellow solid (1.74 g, 74%), m.p. 137-139° C. $\delta_H$ (CDCl$_3$) 7.75-7.68 (2H, m, Ar), 7.54-7.44 (3H, m, Ar), 7.34-7.19 (8H, m, Ar), 7.14-7.07 (2H, m, Ar), 3.54 (2H, q, CH$_2$, J 7.2) and 0.65 (3H, t, CH$_3$, J 7.2)

c) 3,5,6-triphenyl-1H-furo[3,4-c]pyrrole-1,4(5H)-dione (18)

Benzoyl pyrrolinone ester 17 (74 mg) was irradiated with microwave radiation (at 300 Watts) without solvent, heating to 200° C. for 10 minutes. The crude product was then allowed to cool, methanol was added and the solid filtered off and washed with methanol. This gave the furopyrrole 18 as an orange solid (34 mg, 52%), m.p 230-232° C. (lit. [H. Langhals, T. Grundei, T. Potrawa, K. Polborn, *Liebigs Ann. Chem.*, 1996, 679] 230-232° C.). $\delta_H$ (CDCl$_3$) 8.48-8.42 (2H, m, Ar—H) and 7.61-7.20 (13H, m, Ar—H)

d) 2,3,5,6-Tetraphenyl-2,5-dihydropyrrolo[3,4-c]pyrrole-1,4-dione (19)

Can be prepared starting from the intermediate 18 as described in H. Langhals, T. Grundei, T. Potrawa, K. Polborn, *Liebigs Ann. Chem.*, 1996, 679.

e) 2,3,6-triphenylpyrrolo[3,4-c]pyrrole-1,4-dione (21)

N-phenyl pyrrolinone ester 16 (663 mg, 2.16 mmol) and benzonitrile (446 mg, 440 μl, 4.3 mmol) were added successively to a solution of sodium t-amyl oxide [from sodium (150 mg, 6.5 mmol) and t-amyl alcohol (4.0 ml)], and the mixture heated to reflux for 6 hours. The mixture was then cooled, and acidified (dilute aqueous HCl) and extracted with dichloromethane. The organic extracts were then dried and the solvent evaporated. Precipitation from methanol, followed by filtraton gave the triphenyl pyrrolopyrrole 21 as a bright orange solid (18 mg, 3%), m.p. 390° C. (decomp). $\delta_H$ (DMSO d$_6$) 11.54 (1H, s, NH), 8.55 (2H, m, Ar—H), 7.57-7.67 (5H, m, Ar—H), 7.38-7.54 (6H, m, Ar—H), 7.29-7.33 (2H, m, Ar—H; m/z (LCMS) 363.96 (30%, M), 362.95 (100%, M-H); $\lambda_{max}$ abs (DMSO)/nm 269 (ε/24,550), 303 (15,720) 470 (22,580) and 498 (23,640)

The invention claimed is:

1. A process for the preparation of furopyrroles of the general formula

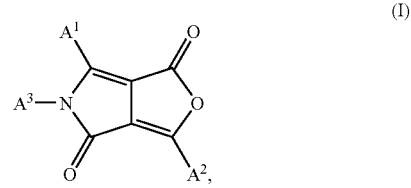

(I)

comprising
(a) microwave irradiation of a compound of the formula

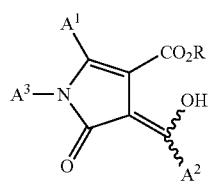
(II)

optionally in the presence of an inert solvent,
wherein $A^1$ and $A^2$ are $C_1$-$C_{18}$alkyl, $C_2$-$C_{18}$alkenyl, $C_2$-$C_{18}$alkynyl, $C_5$-$C_8$cycloalkyl, $C_5$-$C_8$cycloalkenyl, aryl or heteroaryl, $A^3$ is hydrogen, $C_1$-$C_{18}$alkyl, cyanomethyl, $A^3$, —$CR^{30}R^{31}$—$(CH_2)_m$—$A^3$ or Y—$R^{32}$, wherein $R^{30}$ and $R^{31}$ independently of each other stand for hydrogen or $C_1$-$C_4$alkyl, or phenyl which can be substituted up to three times with $C_1$-$C_4$alkyl, $Ar^3$ stands for aryl, $C_5$-$C_8$cycloalkyl, $C_5$-$C_8$cycloalkenyl or heteroaryl, which can be substituted one to three times with $C_1$-$C_8$alkyl, $C_1$-$C_8$alkoxy, halogen or phenyl, which can be substituted with $C_1$-$C_8$alkyl or $C_1$-$C_8$alkoxy one to three times, and m stands for 0, 1, 2, 3 or 4, R is $C_1$-$C_{18}$alkyl, aryl, or aralkyl, in which can be substituted one to three times with $C_1$-$C_8$alkyl, $C_1$-$C_8$alkoxy, or halogen, Y is —C(O)—, —C(O)O—, —C(O)NH—, —$SO_2$NH— or —$SO_2$— and $R^{32}$ is $C_1$-$C_{18}$alkyl, $Ar^3$, or aralkyl.

2. The process according to claim 1, comprising in addition reacting a compound of formula I with a primary amine of the formula $A^4$-$NH_2$ (IV), wherein a DPP of formula

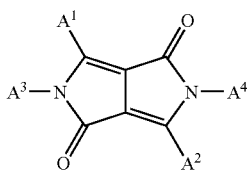
III is obtained,
wherein $A^4$ is $C_1$-$C_{18}$alkyl or $Ar^3$, wherein $Ar^3$, $A^1$, $A^2$ and $A^3$ are defined as in claim 1.

3. The process according to claim 1, wherein the compound of the formula I, wherein $A^3$ is different from a hydrogen atom, is obtained by reacting a compound of the formula

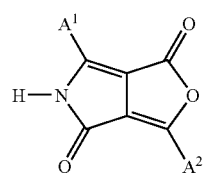
(Ia)

with a compound of the formula $A^3$-X (V), wherein $A^1$, $A^2$ and $A^3$ have the meanings as given in claim 1 and X is a leaving group.

4. The process according to claim 1, wherein $A^1$ and $A^2$ are radicals of the formula

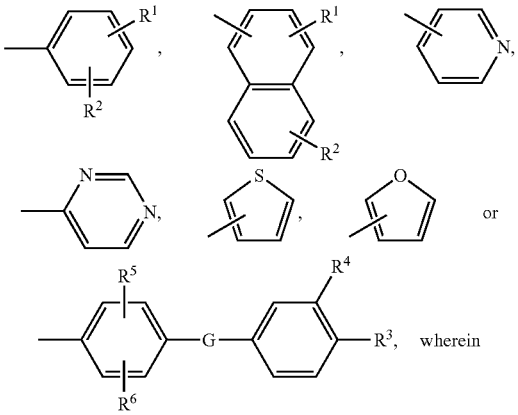

$R^1$ and $R^2$ are independently of each other hydrogen, halogen, $C_1$-$C_{18}$alkyl, $C_1$-$C_{18}$alkoxy, $C_1$-$C_{18}$alkylmercapto, $C_1$-$C_{18}$alkylamino, $C_1$-$C_{18}$alkoxycarbonyl, $C_1$-$C_{18}$alkylaminocarbonyl, —CN, —$NO_2$, trifluoromethyl, $C_5$-$C_8$cycloalkyl, —C≡N—($C_1$-$C_{18}$alkyl), phenyl,

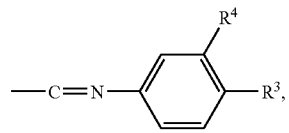

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, —$CONX^5X^6$, —C(O)$OX^7$ or —$SO_2X^9$; wherein $X^5$ and $X^6$ are hydrogen, linear or branched $C_{1-10}$-alkyl, $C_{5-10}$-cycloalkyl or $C_{6-10}$-aryl, $X^7$ is hydrogen, linear or branched $C_{1-10}$-alkyl, $C_{5-10}$-cycloalkyl or $C_{6-10}$-aryl, $X^9$ is hydrogen, linear or branched $C_{1-10}$-alkyl, $C_{5-10}$-cycloalkyl, $C_{7-10}$-aralkyl, $C_{6-10}$-aryl or —$NX^{10}X^{11}$, wherein $X^{10}$ and $X^{11}$ are hydrogen, linear or branched $C_{1-10}$-alkyl, $C_{7-10}$-aralkyl or $C_{6-10}$-aryl, G is —$CH_2$—, —CH($CH_3$)—, —C($CH_3$)$_2$—, —CH=N—, —N=N—, —O—, —S—, —SO—, —$SO_2$—, —$SO_2$NH—, —CONH— or —$NR^7$—, $R^3$ and $R^4$ are independently of each other hydrogen, halogen, $C_1$-$C_6$alkyl, $C_1$-$C_{18}$alkoxy or —CN, $R^5$ and $R^6$ are independently of each other hydrogen, halogen or $C_1$-$C_6$alkyl, and $R^7$ is hydrogen or $C_1$-$C_6$alkyl;

or $A^1$ and $A^2$ are radicals of the formula

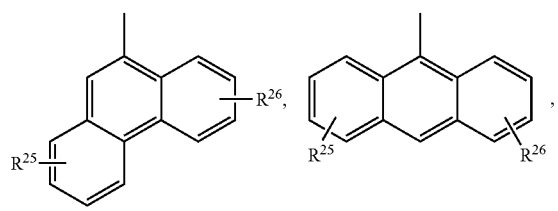

-continued

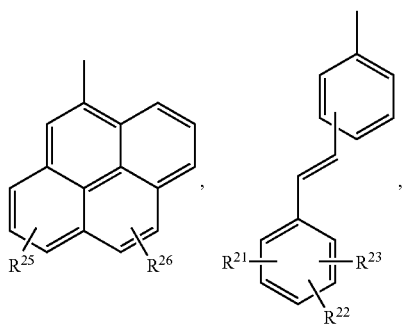,
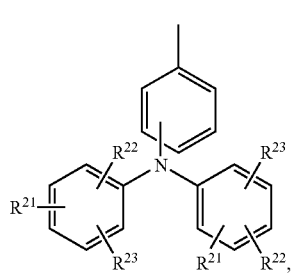,

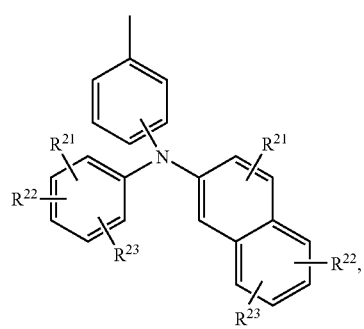,

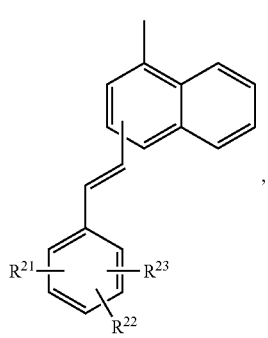,

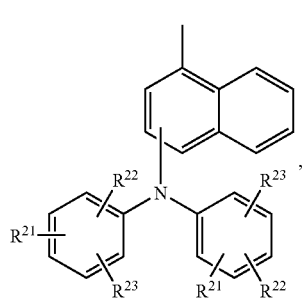,

-continued

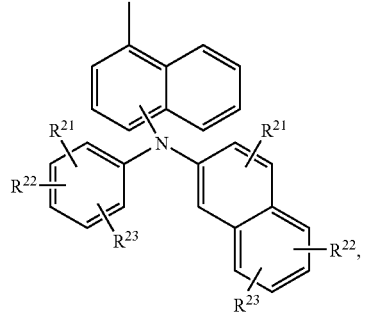,

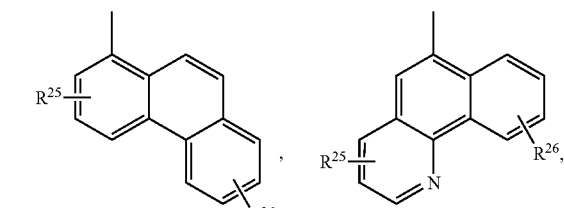,

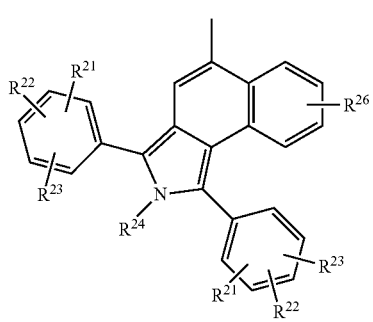 or

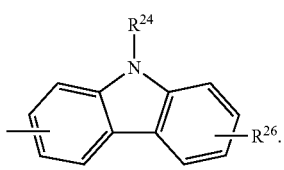.

wherein $R^{21}$, $R^{22}$, $R^{23}$, $R^{25}$ and $R^{26}$ are independently of each other hydrogen, $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group and $R^{24}$ is a $C_1$-$C_6$alkyl group.

5. The process according to claim 4, wherein $A^1$ and $A^2$ are radicals of the formula

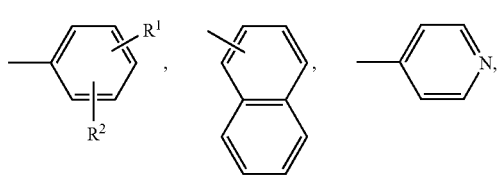

-continued

[pyridyl structure] or [biphenyl structure with R³, R⁴]

wherein $R^1$ and $R^2$ are independently of each other hydrogen, chloro, bromo, $C_1$-$C_4$alkyl, $C_1$-$C_6$alkoxy, $C_1$-$C_6$alkylamino, phenyl or CN, G is —O—, —NR⁷—, —N=N— or —SO$_2$—, $R^3$ and $R^4$ are hydrogen, and $R^7$ is hydrogen, methyl or ethyl.

6. The process according to claim 4, wherein $A^3$ is cyanomethyl, $C_1$-$C_8$alkyl, Y—$R^{32}$ wherein Y is —C(O)— and $R^{32}$ is

[structure with $R^{40}$], wherein $R^{40}$ is $C_1$-$C_4$alkyl, —O—$C_1$-$C_4$alkyl, or —S—$C_1$-$C_4$alkyl, or —(CH$_2$)$_m$—Ar wherein m is 1 and Ar is a group of the formula

[phenyl, naphthyl, or biphenyl structures], which can be substituted one to three times with $C_1$-$C_8$alkyl, $C_1$-$C_8$alkoxy, halogen or phenyl.

7. The process according to claim 4, wherein $A^4$ is

[phenyl, naphthyl, or biphenyl structures], which can be substituted one to three times with $C_1$-$C_8$alkyl, $C_1$-$C_8$alkoxy, halogen or phenyl.

8. The process according to claim 1, wherein the starting compound of formula (II)

[structure (II)]

is obtained by reacting a compound of formula (VIII) with an acyl halide $A^2$-COX:

[structure VIII → structure II via $A^2$—COX]

wherein R, $A^1$ and $A^2$ have the same meaning as given in claim 1, $A^3$ is aryl, and X is halogen.

9. The process according to claim 8, wherein the compound of formula (VIII) is obtained by reacting a compound of formula (IIb) with an amine $A^3$-NH$_2$:

[structure IIb → structure VIII via $A^3$—NH$_2$]

wherein R and $A^1$ have the same meaning as given in claim 1 and $A^3$ is aryl.

10. A process according to claim 1, wherein R is $C_1$-$C_4$alkyl, phenyl, or benzyl, which can be substituted one to three times with $C_1$-$C_8$alkyl, $C_1$-$C_8$alkoxy, or halogen.

11. A process according to claim 5, wherein $A^3$ is cyanomethyl, $C_1$-$C_8$alkyl, Y—$R^{32}$ wherein Y is —C(O)— and $R^{32}$ is

[structure with $R^{40}$], wherein $R^{40}$ is $C_1$-$C_4$alkyl, —O—$C_1$-$C_4$alkyl, or —S—$C_1$-$C_4$alkyl, or —(CH$_2$)$_m$—Ar wherein m is 1 and Ar is a group of the formula

[phenyl, naphthyl, or biphenyl structures], which can be substituted one to three times with $C_1$-$C_8$alkyl, $C_1$-$C_8$alkoxy, halogen or phenyl.

12. A process for the preparation of furopyrroles according to claim 1 wherein $A^1$ and $A^2$ are aryl and $A^3$ is hydrogen, $C_1$-$C_{18}$alkyl, cyanomethyl, Ar³, —CR$^{30}$R$^{31}$—(CH$_2$)$_m$—Ar³ or Y—$R^{32}$, wherein $R^{30}$ and $R^{31}$ independently of each other stand for hydrogen or $C_1$-$C_4$alkyl, or phenyl which can be substituted up to three times with $C_1$-$C_4$alkyl, Ar³ stands for aryl, C₅-C₈cycloalkyl or C₅-C₈cycloalkenyl, which can be substituted one to three times with C₁-C₈alkyl, C₁-C₈alkoxy, halogen or phenyl, which can be substituted with C₁-C₈alkyl or C₁-C₈alkoxy one to three times, and m stands for 0, 1, 2, 3 or 4.

13. The process according to claim 12, comprising in addition reacting a compound of formula I with a primary amine of the formula A⁴-NH₂ (IV), wherein a DPP of formula

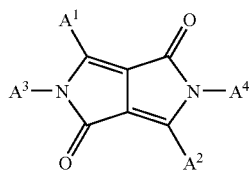

III is obtained,
wherein A⁴ is C₁-C₁₈alkyl or A³.

14. The process according to claim 12, wherein the compound of the formula I, wherein A³ is different from a hydrogen atom, is obtained by reacting a compound of the formula

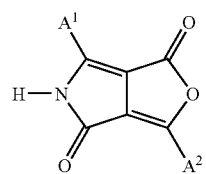

with a compound of the formula A³-X (V), wherein X is a leaving group.

15. The process according to claim 12, wherein A¹ and A² are radicals of the formula

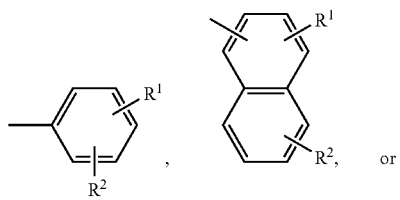

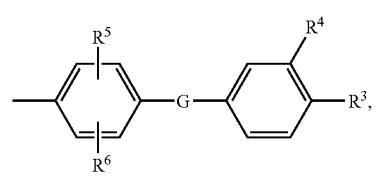

wherein
R¹ and R² are independently of each other hydrogen, halogen, C₁-C₁₈alkyl, C₁-C₁₈alkoxy, C₁-C₁₈alkylmercapto, C₁-C₁₈alkylamino, C₁-C₁₈alkoxycarbonyl, C₁-C₁₈alkylaminocarbonyl, —CN, —NO₂, trifluoromethyl, C₅-C₈cycloalkyl, —C=N—(C₁-C₁₈alkyl), phenyl,

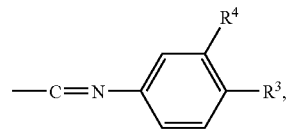

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, —CONX⁵X⁶, —C(O)OX⁷ or —SO₂X⁹; wherein X⁵ X⁶ are hydrogen, linear or branched C₁₋₁₀-alkyl, C₅₋₁₀-cycloalkyl or C₆₋₁₀-aryl, X⁷ is hydrogen, linear or branched C₁₋₁₀-alkyl, C₅₋₁₀-cycloalkyl or C₆₋₁₀-aryl, X⁹ is hydrogen, linear or branched C₁₋₁₀-alkyl, C₅₋₁₀-cycloalkyl, C₇₋₁₀-aralkyl, C₆₋₁₀-aryl or —NX¹⁰X¹¹, wherein X¹⁰ and X¹¹ are hydrogen, linear or branched C₁₋₁₀-alkyl, C₇₋₁₀-aralkyl or C₆₋₁₀-aryl,
G is —CH₂—, —CH(CH₃)—, —C(CH₃)₂—, —CH=N—, —N=N—, —O—, —S—, —SO—, —SO₂—, —SO₂NH—, —CONH— or —NR⁷—,
R³ and R⁴ are independently of each other hydrogen, halogen, C₁-C₆alkyl, C₁-C₁₈alkoxy or —CN,
R⁵ and R⁶ are independently of each other hydrogen, halogen or C₁-C₆alkyl, and R⁷ is hydrogen or C₁-C₆alkyl;
or A¹ and A² are radicals of the formula

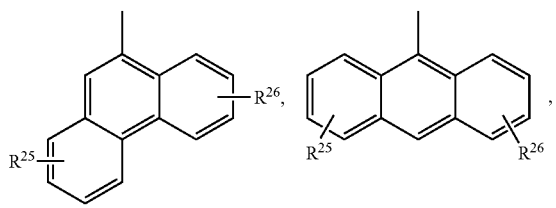

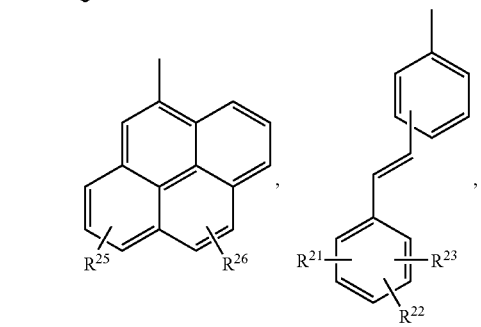

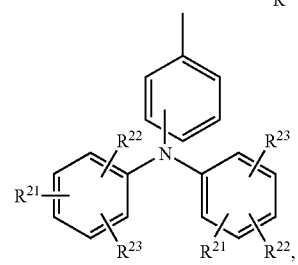

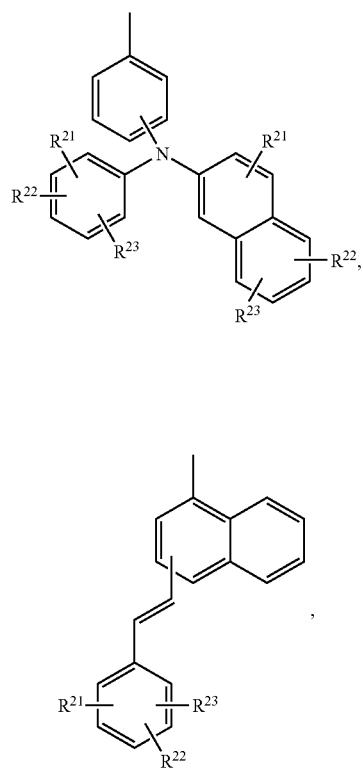

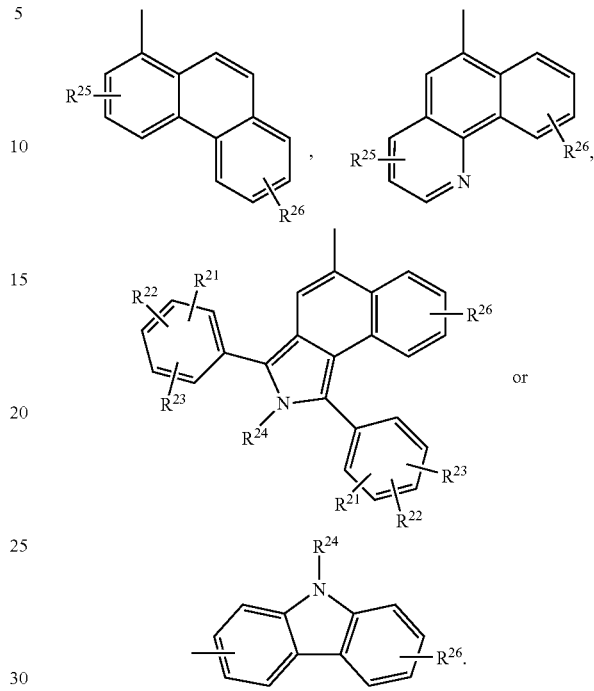

wherein $R^{21}$, $R^{22}$, $R^{23}$, $R^{25}$ and $R^{26}$ are independently of each other hydrogen, $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group and $R^{24}$ is a $C_1$-$C_6$alkyl group.

16. The process according to claim 15, wherein $A^1$ and $A^2$ are radicals of the formula

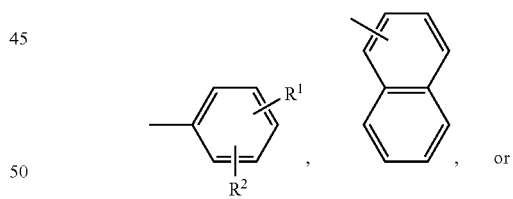

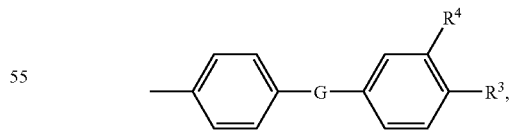

wherein $R^1$ and $R^2$ are independently of each other hydrogen, chloro, bromo, $C_1$-$C_4$alkyl, $C_1$-$C_6$alkoxy, $C_1$-$C_6$alkylamino, phenyl or CN, G is —O—, —$NR^7$—, —N=N— or —$SO_2$—, $R^3$ and $R^4$ are hydrogen, and $R^7$ is hydrogen, methyl or ethyl.

17. The process according to claim 15, wherein $A^3$ is cyanomethyl, $C_1$-$C_8$alkyl, Y—$R^{32}$ wherein Y is —C(O)— and $R^{32}$ is

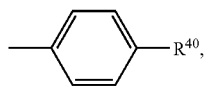

wherein $R^{40}$ is $C_1$-$C_4$alkyl, —O—$C_1$-$C_4$alkyl, or —S—$C_1$-$C_4$alkyl, or —(CH$_2$)$_m$—Ar wherein m is 1 and Ar is a group of the formula

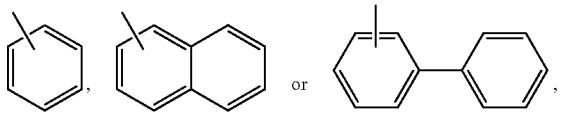

which can be substituted one to three times with $C_1$-$C_8$alkyl, $C_1$-$C_8$alkoxy, halogen or phenyl.

18. The process according to claim 15, wherein $A^4$ is

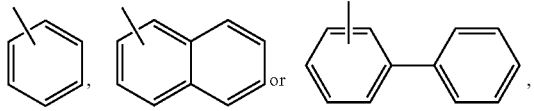

which can be substituted one to three times with $C_1$-$C_8$alkyl, $C_1$-$C_8$alkoxy, halogen or phenyl.

19. A process according to claim 12, wherein R is $C_1$-$C_4$alkyl, phenyl, or benzyl, which can be substituted one to three times with $C_1$-$C_8$alkyl, $C_1$-$C_8$alkoxy, or halogen.

20. A process according to claim 16, wherein $A^3$ is cyanomethyl, $C_1$-$C_8$alkyl, Y—$R^{32}$ wherein Y is —C(O)— and $R^{32}$ is

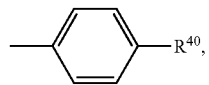

wherein $R^{40}$ is $C_1$-$C_4$alkyl, —O—$C_1$-$C_4$alkyl, or —S—$C_1$-$C_4$alkyl, or —(CH$_2$)$_m$—Ar wherein m is 1 and Ar is a group of the formula

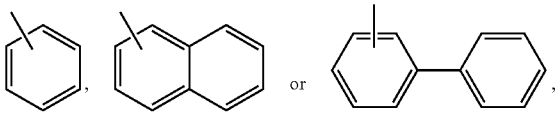

which can be substituted one to three times with $C_1$-$C_8$alkyl, $C_1$-$C_8$alkoxy, halogen or phenyl.

* * * * *